United States Patent
Kang et al.

(10) Patent No.: US 11,840,496 B2
(45) Date of Patent: Dec. 12, 2023

(54) METHOD OF PREPARING L-HOMOSERINE

(71) Applicant: CJ CHEILJEDANG CORPORATION, Seoul (KR)

(72) Inventors: Min Kyu Kang, Seoul (KR); Jung Min Lee, Seoul (KR); Min Sup Kim, Seoul (KR); Il Chul Kim, Seoul (KR); In Sung Lee, Seoul (KR); Jun Young Jung, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/610,731

(22) PCT Filed: Sep. 9, 2020

(86) PCT No.: PCT/KR2020/012178
§ 371 (c)(1),
(2) Date: Nov. 12, 2021

(87) PCT Pub. No.: WO2021/049876
PCT Pub. Date: Mar. 18, 2021

(65) Prior Publication Data
US 2022/0259141 A1     Aug. 18, 2022

(30) Foreign Application Priority Data

Sep. 10, 2019   (KR) .................. 10-2019-0112364

(51) Int. Cl.
*C07C 227/32* (2006.01)
*B01J 31/10* (2006.01)

(52) U.S. Cl.
CPC .............. *C07C 227/32* (2013.01); *B01J 31/10* (2013.01); *B01J 2231/005* (2013.01); *B01J 2531/002* (2013.01)

(58) Field of Classification Search
None
See application file for complete search history.

(56) References Cited

U.S. PATENT DOCUMENTS

| 4,185,027 | A  | 1/1980  | Logan         |
| 5,239,088 | A  | 8/1993  | Hoffman et al.|
| 7,884,240 | B2 | 2/2011  | Hateley et al.|
| 9,834,491 | B2 | 12/2017 | Lee et al.    |
| 2014/0296466 | A1 | 10/2014 | Lee et al. |

FOREIGN PATENT DOCUMENTS

| CN | 101100438 A | 1/2008 |
| CN | 101333175 A | 12/2008 |
| CN | 101374806 A | 2/2009 |
| CN | 106795533 A | 5/2017 |
| CN | 109020854 A | 12/2018 |
| JP | 2012143183 A | 8/2012 |
| KR | 1020140116010 A | 10/2014 |
| SU | 840107 A1 | 6/1981 |
| WO | 2020145627 A1 | 7/2020 |

OTHER PUBLICATIONS

Amberlyst™ 15(H), downloaded from https://www.fishersci.com/shop/products/amberlyst-15-h-ion-exchange-resin-thermo-scientific/AA8907918 on Mar. 20, 2023. (Year: 2023).*
PUROLITE® CT275, downloaded from https://www.purolite.com/product/ct275 on Mar. 20, 2023 (Year: 2023).*
Trilite, downloaded from https://www.samyangtrilite.com/_files/ugd/12e712_b957bfea0c704782860e630be9eda283.pdf?index=true on Mar. 20, 2023, p. 28 (Year: 2023).*
DOWEX(TM), downloaded from https://www.lenntech.com/Data-sheets/Dowex-Monosphere-M-31-L.pdf on Mar. 20, 2023 (Year: 2023).*
English Abstract of CN 101100438, Jan. 9, 2008.
English Abstract of JP 2012-143183, Aug. 2, 2012.
English Abstract of KR 10-2014-0116010, Oct. 1, 2014.
KR NOA dated May 25, 2021 issued in KR 10-2019-0112364.
Rees, D.O., et al., Synthesis of [1,2-13C2, 15N]-l-Homoserine and Its Incorporation by the PKS-NRPS System of Fusarium moniliforme into the Mycotoxin Fusarin C, ChemBioChem, Aug. 2007, 46-50.
English Abstract of Office Action dated Jul. 13, 2022 issued in RU Patent Application No. 2021133096, 6 pp.
English Abstract of SU 840107, 6 pp, Jun. 23, 1981.
Office Action dated Jul. 13, 2022 issued in RU Patent Application No. 2021133096, 6 pp.
English Abstract and Translation of WO 2020-145627, Jul. 16, 2020.
Search Report issued in corresponding SG Patent Application No. 11202112477R, dated Sep. 10, 2019, 3 pp.
Written Opinion issued in corresponding SG Patent Application No. 11202112477R, dated Sep. 10, 2019, 7 pp.
Chinese Office Action for Chinese Patent Application No. 202080039828.1 dated Mar. 20, 2023.

* cited by examiner

*Primary Examiner* — Amy C Bonaparte
(74) *Attorney, Agent, or Firm* — CANTOR COLBURN LLP

(57) ABSTRACT

Provided is a method of preparing L-homoserine, the method including contacting an L-homoserine derivative with a solid acid catalyst.

15 Claims, No Drawings

METHOD OF PREPARING L-HOMOSERINE

CROSS-REFERENCE TO RELATED APPLICATIONS

This application is a national stage application of PCT/KR2020/012178, filed on Sep. 9, 2020, which claims priority and the benefit of KR 10-2019-0112364 filed on Sep. 10, 2019, which is hereby incorporated by reference in its entirety.

TECHNICAL FIELD

The present disclosure relates to a method of preparing L-homoserine.

BACKGROUND ART

Compounds used in industry are materials obtained mainly from petrochemical processes using fossil fuels. Petrochemical processes produce by-products that are harmful to the environment, and fossil fuel reserves are limited.

For this reason, researches have been attempted to supply compounds used in the industry in a sustainable manner by replacing the existing petrochemical processes using fossil fuels.

It is possible to produce various compounds through biosynthesis by fermentation of microorganisms using sugars derived from plant systems. For example, compounds such as methionine, threonine, isoleucine, etc. are produced by biosynthesis.

Meanwhile, homoserine is used in various reactions, such as being used as an intermediate in biosynthesis of methionine, threonine, isoleucine, etc.

Accordingly, a method of simply preparing homoserine is required.

DESCRIPTION OF EMBODIMENTS

Technical Problem

An aspect of the present disclosure is to provide a method of simply preparing L-homoserine with high purity at a high recovery rate.

Solution to Problem

According to an aspect,

The present disclosure provides a method of preparing L-homoserine, the method including contacting an L-homoserine derivative represented by the following Formula 1 with a solid acid catalyst:

<Formula 1>

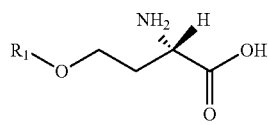

in Formula 1

$R_1$ is $R_a$—(C=O)—, $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, and substituents of the alkyl group, the alkenyl group, the alkynyl group, the cycloalkyl group, the aryl group, and the heteroaryl group are each independently halogen, a carboxyl group (—COOH), an acetyl group (—COCH$_3$), an amino group (—NH$_2$), a nitro group (—NO$_2$), a cyano group (—CN), an alkyl group having 1 to 6 carbon atoms, an aryl group having 6 to 10 carbon atoms, or a cycloalkyl group having 3 to 10 carbon atoms.

Advantageous Effects of Disclosure

According to a method of preparing L-homoserine according to one embodiment of the present disclosure, it is possible to simply prepare L-homoserine with high purity at a high recovery rate by using a solid acid catalyst.

Further, according to the method of preparing L-homoserine according to one embodiment of the present disclosure, production efficiency is remarkably improved, recycling of the catalyst is easy, and maintenance costs are reduced, thereby securing economic efficiency.

BEST MODE

Hereinafter, a method of preparing L-homoserine according to one embodiment of the present disclosure will be described in more detail.

While the inventive concept of the present disclosure described below is susceptible to various modifications and has many embodiments, specific embodiments will be illustrated and described in detail in the detailed description. It should be understood, however, that the description is not intended to limit the inventive concept of the present disclosure to particular embodiments, but on the contrary, the intention is to cover all modifications, equivalents, or alternatives falling within the technical scope of the inventive concept of the present disclosure.

In the present disclosure, terms such as first, second, third, fourth, etc. may be used to describe various components, but the components should not be limited by these terms. The terms are used only to distinguish one component from another component.

As used herein, the term 'L-homoserine' is an L-isomer of homoserine.

As used herein, the term 'D-homoserine' is a D-isomer of homoserine.

As used herein, the term "% enantiomeric excess (% ee)" refers to purity of an enantiomer of a sample, i.e., a percentage of one enantiomer in greater amounts than the other in a sample. For example, % enantiomeric excess of L-homoserine refers to a percentage of L-homoserine in greater amounts than D-homoserine in homoserine. For example, % enantiomeric excess of L-homoserine is represented by the following Equation 1:

% Enantiomeric excess of L-homoserine=[(amount of L-homoserine−amount of D-homoserine)/(amount of L-homoserine+amount of D-homoserine)]×100      Equation 1

The method of preparing L-homoserine according to one embodiment may include contacting an L-homoserine derivative represented by Formula 1 with a solid acid catalyst:

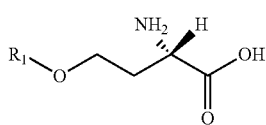

<Formula 1> in Formula 1,

R₁ is $R_a$—(C=O)—, $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, and substituents of the alkyl group, the alkenyl group, the alkynyl group, the cycloalkyl group, the aryl group, and the heteroaryl group are each independently halogen, a carboxyl group (—COOH), an acetyl group (—COCH₃), an amino group (—NH₂), a nitro group (—NO₂), a cyano group (—CN), an alkyl group having 1 to 6 carbon atoms, an aryl group having 6 to 10 carbon atoms, or a cycloalkyl group having 3 to 10 carbon atoms.

For example, the method of preparing L-homoserine may include preparing L-homoserine represented by the following Formula 2 by hydrolysis of the L-homoserine derivative represented by the following Formula 1 in the presence of the solid acid catalyst:

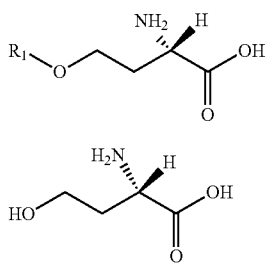

<Formula 1>

<Formula 2> in the above Formulae,

R₁ is $R_a$—(C=O)—, $R_a$ is a substituted or unsubstituted alkyl group having 1 to 6 carbon atoms, a substituted or unsubstituted alkenyl group having 1 to 6 carbon atoms, a substituted or unsubstituted alkynyl group having 1 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, and substituents of the alkyl group, the alkenyl group, the alkynyl group, the cycloalkyl group, the aryl group, and the heteroaryl group are each independently halogen, a carboxyl group (—COOH), an acetyl group (—COCH₃), an amino group (—NH₂), a nitro group (—NO₂), a cyano group (—CN), an alkyl group having 1 to 6 carbon atoms, an aryl group having 6 to 10 carbon atoms, or a cycloalkyl group having 3 to 10 carbon atoms.

Such a method of preparing L-homoserine of the present disclosure is able to simply prepare L-homoserine with high purity at a high recovery rate by using an L-homoserine derivative as a starting material and a solid acid catalyst.

In the L-homoserine derivative represented by Formula 1 of the present disclosure, $R_e$ may be, for example, methyl (—CH₃), carboxyethyl (—CH₂CH₂COOH), acetylethyl (—CH₂CH₂(C=O)CH₃), 2-pyrazinyl (—C₄H₃N₂), 2-amino-5-pyridinyl (—C₆H₃N—NH₂)), 4-pyridinyl (—C₆H₄N), or (3-amino-5-methyl)phenyl (—C₆H₃(CH₃)(NH₂)). Particularly, in the L-homoserine derivative represented by Formula 1 of the present disclosure, R₄ may be, for example, acetyl, or succinyl. Since the L-homoserine derivative represented by Formula 1 of the present disclosure has such a functional group, L-homoserine with improved purity may be more easily prepared.

In contacting the L-homoserine derivative with the solid acid catalyst of the present disclosure, the L-homoserine derivative represented by Formula 1 of the present disclosure may be prepared from, for example, a fermentation broth including the L-homoserine derivative. Therefore, by using the L-homoserine derivative represented by Formula 1 which is produced during a fermentation process, it is possible to efficiently prepare L-homoserine. In other words, the method of the present disclosure may further include preparing the L-homoserine derivative from the fermentation broth including the L-homoserine derivative, before contacting the L-homoserine derivative with the solid acid catalyst of the present disclosure. The preparing the L-homoserine derivative from the fermentation broth including the L-homoserine derivative of the present disclosure may include removing cells from the fermentation broth including the L-homoserine derivative through a membrane filter. By removing cells from the fermentation broth including the L-homoserine derivative of the present disclosure through the membrane filter, an aqueous solution including the L-homoserine derivative of the present disclosure may be prepared.

As used herein, the term 'fermentation broth including the L-homoserine derivative' may be a fermentation broth including the L-homoserine derivative produced during the fermentation process. The fermentation broth may be a fermentation broth obtained by culturing microorganisms in a medium containing sugars, or a fermentation broth obtained by enzymatic conversion of a fermentation broth obtained by culturing microorganisms. For example, the fermentation broth including the L-homoserine derivative of the present disclosure may be a fermentation broth including the L-homoserine derivative directly produced by culturing microorganisms in a medium containing sugars, or a fermentation broth including the L-homoserine derivative, which is obtained by enzymatic conversion of amino acids produced by culturing microorganisms in a medium containing sugars. The kind of the microorganisms used in preparing the fermentation broth including the L-homoserine derivative of the present disclosure is not particularly limited, and any microorganisms in the art may be used as long as they are able to produce the L-homoserine derivative by direct fermentation or enzymatic conversion.

The L-homoserine derivative represented by Formula 1 of the present disclosure may be, for example, compounds represented by the following Formulae 3 to 8:

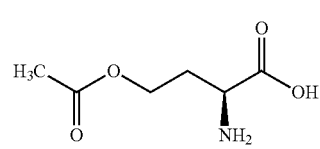

<Formula 3>

<Formula 4>

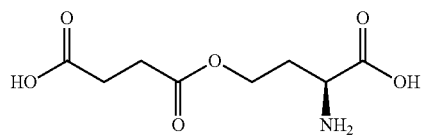

<Formula 5>

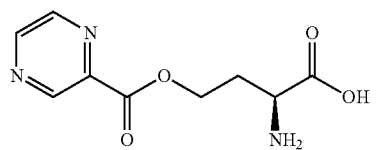

<Formula 6>

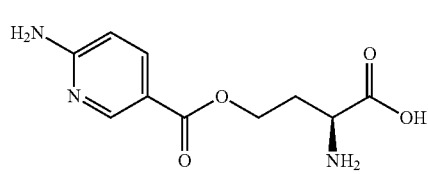

<Formula 7>

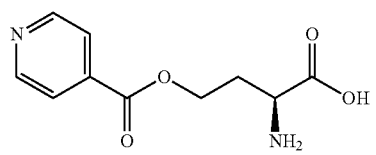

<Formula 8>

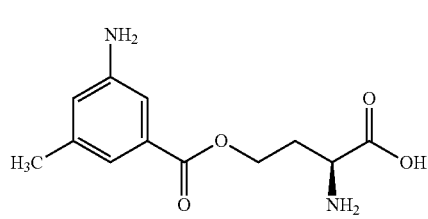

The L-homoserine derivative of the present disclosure may be particularly O-acetyl-L-homoserine or O-succinyl-L-homoserine, but is not limited thereto. Any derivative is possible as long as it is a derivative in which a substituent is linked to a terminal oxygen of L-homoserine obtained during fermentation and known in the art. The fermentation broth including the L-homoserine derivative of the present disclosure may be, for example, a fermentation broth obtained by fermentation of a medium including CJM-BTJ/pCJ-MetA-CL (Accession No. KCCM-10872) which is an O-succinyl-L-homoserine-producing strain or CJM-BTJA/pCJ-MetX-CL (Accession No. KCCM-10873) which is an O-acetyl-L-homoserine-producing strain, as disclosed in Example 2 of KR 10-2014-0116010.

The contacting of the L-homoserine derivative with the solid acid catalyst of the present disclosure may be, for example, contacting of the L-homoserine derivative with water and the solid acid catalyst.

The water may be, for example, pure water such as distilled water, etc., but is not limited to such pure water, may include a composition including water as a main component. A content of water included in the composition including water as a main component may be, for example, 50% by weight to 100% by weight, 60% by weight to 100% by weight, 70% by weight to 100% by weight, 80% by weight to 100% by weight, 90% by weight to 100% by weight, 95% by weight to 100% by weight, or 99% by weight to 100% by weight, based on the total weight of the composition.

The solid acid catalyst of the present disclosure refers to a catalyst which is not dissolved in a solvent and maintains a solid state even when mixed with a solvent.

The solid acid catalyst of the present disclosure may include a resin catalyst. Specifically, the solid acid catalyst of the present disclosure may include, for example, a cation exchange resin catalyst.

The cation exchange resin catalyst of the present disclosure has a structure in which an acidic functional group is linked to a polymer. Since the cation exchange resin catalyst of the present disclosure includes the acidic functional group, the acidic functional group may serve as the acid catalyst.

The cation exchange resin catalyst of the present disclosure may include a polymer, and specifically, the polymer may be a copolymer in which divinyl benzene is crosslinked to polystyrene, or a polystyrene homopolymer, but is not limited thereto, and any polymer may be included as long as it may be used as the cation exchange resin catalyst in the art. When catalytic activity of the cation exchange resin catalyst of the present disclosure is reduced due to long-term use thereof, the cation exchange resin catalyst may be reused through a recycling process without exchanging the catalyst.

The cation exchange resin catalyst of the present disclosure may include, for example, one or more acidic functional groups selected from —$SO_3H$ and —COOH. When the cation exchange resin catalyst of the present disclosure includes the acidic functional group, it may serve as the acidic catalyst. A cation exchange resin catalyst including —$SO_3H$ functional group of the present disclosure is strongly acidic. The strongly acidic catalyst is, for example, at pH of less than 1 to 5. A cation exchange resin catalyst including —COOH functional group of the present disclosure is weakly acidic. The weakly acidic catalyst is, for example, at pH of less than 5 to 7.

The cation exchange resin catalyst of the present disclosure may have, for example, a structure in which one or more acidic functional groups selected from —$SO_3H$ and —COOH are linked to a polystyrene-divinylbenzene copolymer.

Commercially available cation exchange resin catalysts may include, for example, Amberlyst 15, Purolite CT275, TRILITE SPC160H, DOWEX M-31(H), etc., but the cation exchange resin catalysts of the present disclosure are not limited thereto. Any cation exchange resin catalyst may be used as long as it is used as the cation exchange resin catalyst in the art.

The cation exchange resin catalyst of the present disclosure may be, for example, in a particle shape. The size of the particle may be, for example, 0.1 mm to 10 mm, 0.1 mm to 5 mm, 0.1 mm to 4 mm, 0.1 mm to 3 mm, 0.1 mm to 2 mm, or 0.1 mm to 1 mm. The particle may be, for example, a porous particle. The average diameter of the pores included in the porous particle may be 10 nm to 500 nm, 10 nm to 200 nm, 10 nm to 100 nm, 10 nm to 90 nm, 20 nm to 80 nm, or 30 nm to 70 nm. The total volume of the pores included in the cation exchange resin catalyst of the present disclosure may be 0.1 mL/g to 10 mL/g, 0.1 mL/g to 5 mL/g, 0.1 mL/g to 2 mL/g, 0.1 mL/g to 1 mL/g, 0.1 mL/g to 0.90 mL/g, 0.2 mL/g to 0.8 mL/g, 0.3 mL/g to 0.7 mL/g, or 0.4 mL/g to 0.6 mL/g. When the cation exchange resin catalyst has such a particle size, pore diameter and/or total pore volume, L-homoserine may be prepared with a more improved yield.

The contacting of L-homoserine derivative with the solid acid catalyst of the present disclosure may be carried out in a resin tower including the cation exchange resin catalyst.

The method of the present disclosure may further include carrying out hydrolysis of the L-homoserine derivative after or concurrently with the contacting.

The resin tower of the present disclosure may be a tower inside which the cation exchange resin catalyst is filled. Specifically, hydrolysis of the L-homoserine derivative may be carried out in the resin tower of the present disclosure. A method of placing the cation exchange resin catalyst in the resin tower of the present disclosure is not particularly limited. The volume occupied by the cation exchange resin catalyst in the resin tower of the present disclosure may be, for example, 10% or more, 20% or more, 30% or more, 40% or more, 50% or more, 60% or more, 70% or more, 80% or more, or 90% or more of the total internal volume of the resin tower.

The content of the cation exchange resin catalyst of the present disclosure may be, for example, 0.1 equivalent to 10 equivalents, 0.1 equivalent to 5 equivalents, 0.1 equivalent to 4 equivalents, 0.1 equivalent to 3 equivalents, 0.1 equivalent to 2 equivalents, 0.1 equivalent to 1.5 equivalents, 0.1 equivalent to 1.3 equivalents, or 0.1 equivalent to 1.2 equivalents with respect to 1 equivalent of the L-homoserine derivative represented by Formula 1. When the content of the cation exchange resin catalyst of the present disclosure is 0.1 equivalent or more with respect to 1 equivalent of the L-homoserine derivative, the catalyst may increase a reaction rate. On the contrary, when the content of the cation exchange resin catalyst is −10 equivalents or less with respect to 1 equivalent of the L-homoserine derivative, by-products may be increased, and thus it may be prevented that a separate purification process is involved, and the purity/yield of a final target product is lowered.

In contacting of the L-homoserine derivative with the solid acid catalyst of the present disclosure, the aqueous solution including the solid acid catalyst of the present disclosure may have pH of 1 to 5, 1 to 4.5, 1 to 4.0, 1 to 3.5, 2 to 5, 2 to 4.5, 2 to 4.0, 2 to 3.5, 3 to 5, 3 to 4.5, or 3 to 3.5. When the aqueous solution including the cation exchange resin catalyst of the present disclosure has the above range of pH, hydrolysis may effectively occur.

In preparing L-homoserine using the cation exchange resin catalyst of the present disclosure, the contacting may be carried out at a temperature of, for example, 20° C. to 150° C., 20° C. to 140° C., 20° C. to 130° C., 20° C. to 120° C., 40° C. to 110° C., 50° C. to 100° C., 60° C. to 90° C., or 70° C. to 90° C. In preparing L-homoserine using the cation exchange resin catalyst, the contacting may be carried out for, for example, 0.1 hr to 30 hr, 0.5 hr to 20 hr, 1 hr to 10 hr, 2 hr to 8 hr, 3 hr to 7 hr, or 4 hr to 6 hr. In other words, preparing L-homoserine may be carried out with an aqueous solution, comprising the L-homoserine derivative, which has a temperature of 20° C. to 150° C. and a residence time of 0.1 hr to 20 hr in the resin tower. When hydrolysis may be carried out within the above ranges of temperature and time, L-homoserine may be more easily prepared.

In contacting the L-homoserine derivative with the solid acid catalyst of the present disclosure, a pressure in the resin tower may be, for example, 0.01 atm to 1 atm, 0.05 atm to 1 atm, 0.1 atm to 1 atm, or 0.5 atm to 1 atm. The pressure in the resin tower may be, for example, 1 atm.

The contacting of the L-homoserine derivative with the solid acid catalyst of the present disclosure may include supplying the L-homoserine derivative; producing L-homoserine by contacting the L-homoserine derivative with the solid acid catalyst; and/or discharging the L-homoserine.

The contacting of the L-homoserine derivative with the solid acid catalyst of the present disclosure may more specifically include supplying a first composition including the L-homoserine derivative to the resin tower; producing a second composition including L-homoserine by hydrolysis of the first composition including the L-homoserine derivative in the resin tower in the presence of the solid acid catalyst; and/or discharging the second composition including L-homoserine from the resin tower. In the supplying of the first composition including the L-homoserine derivative to the resin tower, the first composition including the L-homoserine derivative may be supplied from a supply tank. Since large quantities of the L-homoserine derivative may be supplied using the supply tank and/or the resin tower, a large quantity of hydrolysis may be carried out in a short time. The first composition and the second composition of the present disclosure may be substantially liquids. The first composition of the present disclosure may be, for example, an aqueous solution including L-homoserine derivative. The second composition of the present disclosure may be, for example, an aqueous solution including L-homoserine.

The supplying of the first composition to the resin tower and the discharging of the second composition from the resin tower of the present disclosure may be carried out continuously or discontinuously. The term "carried out continuously" may be used interchangeably with "carried out in a continuous mode", and the term "carried out discontinuously" may be used interchangeably with "carried out in a batch mode".

In the continuous mode of the present disclosure, the second composition may be discharged from the resin tower while supplying the first composition to the resin tower of the present disclosure. In the continuous mode of the present disclosure, for example, hydrolysis of the L-homoserine derivative of the present disclosure may be carried out in the resin tower without interruption while supplying the first composition to the resin tower and discharging the second composition from the resin tower.

As compared with the batch mode of the present disclosure, the continuous mode of the present disclosure may continuously produce L-homoserine, and thus production efficiency may be remarkably improved, and the resin catalyst may be recycled only by changing the composition of the supply solution without separation of the resin catalyst. Therefore, recycling of the resin catalyst may be easy in the continuous mode of the present disclosure, as compared with the batch mode requiring separation and purification of the resin catalyst. Consequently, maintenance and/or repair of the overall process become simple and the maintenance cost is reduced, and thus costs of the overall process may be reduced in the continuous mode of the present disclosure, as compared with the batch mode. Therefore, economic efficiency of the overall process of the continuous mode of the present disclosure may be further improved, as compared with that of the batch mode of the present disclosure.

In the batch mode of the present disclosure, the supplying of the first composition to the resin tower and the discharging of the second composition from the resin tower may be discontinuously carried out. In the batch mode, for example, the second composition is not discharged from the resin tower while supplying the first composition to the resin tower. Further, the first composition is not supplied to the resin tower while discharging the second composition from the resin tower. In the batch mode, for example, no hydrolysis of the L-homoserine derivative of the present disclosure may be carried out while supplying the first composition to the resin tower or discharging the second composition from the resin tower.

In addition to the above-described processes, the method of preparing L-homoserine of the present disclosure may further include, for example, collecting L-homoserine of the present disclosure.

In addition to the above-described processes, the method of preparing L-homoserine of the present disclosure may further include preparing a third composition including crystallized L-homoserine by supplying the second composition including L-homoserine to an ageing tank; preparing a fourth composition including separated L-homoserine by supplying the third composition including crystallized L-homoserine to a separator; and/or obtaining dried L-homoserine by supplying the fourth composition including separated L-homoserine to a dryer. When the method of preparing L-homoserine further includes these processes, purity and/or yield of the prepared L-homoserine may be further improved.

In preparing the third composition including crystallized L-homoserine by supplying the second composition including L-homoserine to the ageing tank of the present disclosure, the second composition discharged from the resin tower may be cooled to room temperature in the ageing tank, thereby crystallizing at least a portion of L-homoserine. Therefore, the third composition including L-homoserine crystals, i.e., a slurry solution may be prepared. L-homoserine may be additionally crystalized by adding a non-solvent of L-homoserine to the slurry solution. The non-solvent may be, for example, ethanol.

In preparing the fourth composition including separated L-homoserine by supplying the third composition including crystallized L-homoserine to the separator, the crystallized L-homoserine may be separated using a separator, such as a filter, etc. The fourth composition may include L-homoserine and a small amount of a solvent. The fourth composition may be substantially in a solid state.

In obtaining dried L-homoserine by supplying the fourth composition including separated L-homoserine to the dryer, L-homoserine crystal powder may be obtained with high purity and/or yield by drying the separated L-homoserine.

In the method of preparing L-homoserine of the present disclosure, the yield of L-homoserine to be prepared may be, for example, 10% or more, 20% or more, 30% or more, 40% or more, 50% or more, 60% or more, 70% or more, 80% or more, 90% or more, 95% or more, 96% or more, 97% or more, 98% or more, or 99% or more.

In the method of preparing L-homoserine of the present disclosure, the purity of L-homoserine to be prepared may be, for example, 98% or more, 98.5% or more, 99% or more, 99.1% or more, 99.2% or more, 99.3% or more, 99.4% or more, 99.5% or more, 99.6% or more, 99.6% or more, 99.7% or more, 99.8% or more, or 99.9% or more.

In the method of preparing L-homoserine of the present disclosure, % enantiomeric excess of L-homoserine to be prepared may be, for example, 10% ee or more, 20% ee or more, 30% ee or more, 40% ee or more, 50% ee or more, 60% ee or more, 70% ee or more, 80% ee or more, 90% ee or more, 91% ee or more, 92% ee or more, 93% ee or more, 94% ee or more, 95% ee or more, 96% ee or more, 97% ee or more, 98% ee or more, or 99% ee or more. In the method of preparing L-homoserine, % enantiomeric excess of L-homoserine to be prepared may be, for example, 100% ee.

The preparation of L-homoserine of the present disclosure may be, for example, carried out in an L-homoserine production system for mass production, but is not limited to these exemplary embodiments, and any process, reactor, system, and/or method available in the art may be used.

The L-homoserine production system of the present disclosure may include, for example, a supply tank, a resin tower, a crystallizer, an ageing tank, a separator, and/or a dryer. Alternatively, in the L-homoserine production system, since the ageing tank may also serve as the crystallizer, the crystallizer may be omitted. The L-homoserine production system of the present disclosure may include, for example, a supply tank, a resin tower, a crystallizer, an ageing tank, a separator, and/or a dryer.

The supply tank of the present disclosure may include the first composition including L-homoserine derivative and may supply the first composition to the upper portion of the resin tower. The first composition included in the supply tank may be a composition in which cells are removed. Alternatively, the first composition included in the supply tank may be a fermentation broth. When the supply tank of the present disclosure includes the fermentation broth, a membrane filter may be disposed at the outlet of the supply tank or between the supply tank and the resin tower to remove cells from the fermentation broth.

The resin tower of the present disclosure may include the cation exchange resin catalyst, as described above. When the resin tower of the present disclosure includes the cation exchange resin catalyst, the first composition including L-homoserine derivative in the resin tower may be converted to the second composition including L-homoserine by hydrolysis. The shape of the resin tower is not particularly limited, and any shape used in the art may be used. The temperature of the resin tower of the present disclosure may be, for example, 20° C. to 150° C., 20° C. to 140° C., 20° C. to 130° C., 20° C. to 120° C., 40° C. to 110° C., 50° C. to 100° C., 60° C. to 90° C., or 70° C. to 90° C. The time required for the first composition supplied to the resin tower of the present disclosure to be converted to the second composition and to be discharged from the resin tower may be, for example, 0.1 hr to 30 hr, 0.5 hr to 20 hr, 1 hr to 10 hr, 2 to 8 hr, 3 hr to 7 hr, or 4 hr to 6 hr. A material of the resin tower of the present disclosure may be stainless steel. The material of the resin tower of the present disclosure may be, for example, stainless steel having acid resistance.

The crystallizer of the present disclosure may crystallize at least a portion of L-homoserine included in the second composition. Crystallization may be carried out by reducing the temperature, by adding a non-solvent, or the like. The crystallization time may be 0.1 hr to 30 hr, 0.5 hr to 20 hr, or 1 hr to 10 hr. The crystallization temperature of the present disclosure may be 1° C. to 30° C., 10° C. to 30° C., or 20° C. to 30° C. The crystallizer of the present disclosure may be, for example, a forced circulation evaporator. Specifically, the crystallizer of the present disclosure may include, for example, one or more selected from a vacuum pump, a condenser, an agitator, and a cooling jacket. A material of the crystallizer of the present disclosure may be stainless steel. The material of the crystallizer of the present disclosure may be, for example, stainless steel having acid resistance.

The ageing tank of the present disclosure may stabilize the composition including L-homoserine crystals, and may further facilitates subsequent separation of the L-homoserine crystals in the separator. The ageing time of the present disclosure may be 0.1 hr to 30 hr, 0.5 hr to 20 hr, or 1 hr to 10 hr. The ageing temperature of the present disclosure may be 1° C. to 30° C., 10° C. to 30° C., or 20° C. to 30° C. A material of the ageing tank of the present disclosure may be stainless steel. The material of the ageing tank of the present disclosure may be, for example, stainless steel having acid resistance.

The separator of the present disclosure may separate L-homoserine crystals from the composition including L-homoserine, and the separator of the present disclosure may be, for example, a belt separator, a centrifugal separator, etc.

The dryer of the present disclosure may remove volatile components, such as residual moisture, etc., from the separated L-homoserine crystals. The dryer of the present disclosure may be, for example, an oven, a fluidized bed dryer, etc. The drying temperature may be 20° C. to 100° C., 30° C. to 80° C., or 40° C. to 60° C. The pressure of the dryer of the present disclosure may be 1 atm or less than 1 atm. The drying time of the present disclosure may be 0.1 hr to 30 hr, 0.5 hr to 20 hr, or 1 hr to 10 hr. For example, the fluidized bed dryer of the present disclosure has an advantage that continuous drying is possible.

For example, the preparation of L-homoserine using the L-homoserine production system of the present disclosure may be carried out as follows.

The first composition including the L-homoserine derivative may be supplied from the supply tank to the upper portion of the resin tower. In the resin tower, the first composition including L-homoserine derivative may undergo hydrolysis in the presence of the solid acid catalyst to be converted into the second composition including L-homoserine. The second composition including L-homoserine may be discharged from the lower portion of the resin tower. The second composition discharged from the lower portion of the resin tower may be supplied to the crystallizer. In the crystallizer, at least a portion of L-homoserine included in the second composition may be crystallized. The composition including crystallized L-homoserine may be supplied to the ageing tank and may be stabilized. The stabilized composition may be supplied to the separator, and L-homoserine crystals may be separated in the separator. The separated L-homoserine crystals may be supplied to the dryer to obtain dried L-homoserine powder.

For example, when crystallization and stabilization are simultaneously carried out in the ageing tank, the crystallizer may be omitted.

For example, the preparation of L-homoserine using the L-homoserine production system of the present disclosure may be carried out as follows.

The first composition including the L-homoserine derivative may be supplied from the supply tank to the upper portion of the resin tower. In the resin tower, the first composition including L-homoserine derivative may undergo hydrolysis in the presence of the solid acid catalyst to be converted into the second composition including L-homoserine. The second composition including L-homoserine may be discharged from the lower portion of the resin tower. The second composition discharged from the lower portion of the resin tower may be supplied to the ageing tank. In the ageing tank, at least a portion of L-homoserine included in the second composition may be crystallized, and the composition including the crystallized L-homoserine may be stabilized. The stabilized composition may be supplied to the separator, and L-homoserine crystals may be separated in the separator. The separated L-homoserine crystals may be supplied to the dryer to obtain dried L-homoserine powder. The system and preparation process may be more simplified by incorporating the crystallizer into the ageing tank. The ageing tank incorporated with the crystallizer may have a structure in which one or more devices selected from a vacuum pump, a condenser, an agitator, and a cooling jacket are added to the ageing tank. Due to such a structure, ageing and crystallization may be carried out at the same time.

As used herein, the term "alkyl" may refer to a fully saturated branched or unbranched (or straight or linear) hydrocarbon.

Non-limiting examples of "alkyl" may include methyl, ethyl, n-propyl, isopropyl, n-butyl, isobutyl, sec-butyl, n-pentyl, isopentyl, neopentyl, n-hexyl, 3-methylhexyl, 2,2-dimethylpentyl, 2,3-dimethylpentyl, n-heptyl, etc.

One or more hydrogen atoms in "alkyl" may be substituted with halogen atoms, C1-020 alkyl groups substituted with halogen atoms (e.g., $CCF_3$, $CHCF_2$, $CH_2F$, $CCI_3$, etc.), C1-020 alkoxy, C2-C20 alkoxyalkyl, hydroxy groups, nitro groups, cyano groups, amino groups, amidino groups, hydrazine, hydrazone, carboxyl groups or salts thereof, sulfonyl groups, sulfamoyl groups, sulfonic acid groups or salts thereof, phosphoric acid or salts thereof, C1-020 alkyl groups, C2-C20 alkenyl groups, C2-C20 alkynyl groups, C1-020 heteroalkyl groups, C6-C20 aryl groups, C6-C20 arylalkyl groups, C6-C20 heteroaryl groups, C7-C20 heteroarylalkyl groups, C6-C20 heteroaryloxy groups, C6-C20 heteroaryloxyalkyl groups, or C6-C20 heteroarylalkyl groups.

As used herein, the term "halogen" may include fluorine, bromine, chlorine, iodine, etc.

As used herein, the term "alkoxy" represents "alkyl-O—", and alkyl is as described above. The alkoxy group may be, for example, a methoxy group, an ethoxy group, a 2-propoxy group, a butoxy group, a t-butoxy group, a pentyloxy group, a hexyloxy group, etc. One or more hydrogen atoms in alkoxy may be substituted with the same substituent as in the alkyl group described above.

As used herein, the term "alkenyl" may refer to a branched or unbranched hydrocarbon having at least one carbon-carbon double bond. Non-limiting examples of the alkenyl group may include vinyl, allyl, butenyl, propenyl, isobutenyl, etc., and one or more hydrogen atoms in alkenyl may be substituted with the same substituent as in the alkyl group described above.

As used herein, the term "alkynyl" may refer to a branched or unbranched hydrocarbon having at least one carbon-carbon triple bond. Non-limiting examples of "alkynyl" may include ethynyl, butynyl, isobutynyl, isopropynyl, etc.

One or more hydrogen atoms in the term "alkynyl", as used herein, may be substituted with the same substituent as in the alkyl group described above.

As used herein, the term "aryl" may also include a group in which an aromatic ring is selectively fused to one or more carbon rings. Non-limiting examples of "aryl" may include phenyl, naphthyl, tetrahydronaphthyl, etc. One or more hydrogen atoms in the "aryl" group may be substituted with the same substituent as in the alkyl group described above.

As used herein, the term "heteroaryl" refers to a monocyclic or bicyclic organic group, in which one or more heteroatoms selected from N, O, P, and S are included and the remaining ring atoms are carbon. The heteroaryl group may include, for example, 1-5 heteroatoms and may include 5-10 ring members. The S or N may be oxidized to have many different oxidation states.

Examples of heteroaryl may include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, 2-pyrazin-2-yl, pyrazin-4-yl, pyrazin-5-yl, 2-pyrimidin-2-yl, 4-pyrimidin-2-yl, or 5-pyrimidin-2-yl.

Heteroaryl may include a case where a heteroaromatic ring is selectively fused to one or more aryl, cycloaliphatic, or heterocycles.

MODE OF DISCLOSURE

The present disclosure will be described in more detail with reference to the following Examples and Comparative Examples. However, Examples are intended to illustrate the present disclosure, and the scope of the present disclosure is not limited thereto.

Comparative Example 1: Hydrochloric acid catalyst of 1.02 equivalents

Cells were removed from a fermentation broth, of which culture had been completed, through a membrane filter, and an aqueous solution including O-acetyl-L-homoserine was obtained.

40 mL of the aqueous solution including O-acetyl-L-homoserine (O-acetyl-L-homoserine concentration: 300 g/L, 74.5 mmol) was supplied to a reactor, and then 12.4 mL (76.0 mmol, 1.02 eq) of 6 N HCl was slowly added to the reactor to prepare a reaction solution at pH of 0.1 to 1.0. The prepared reaction solution was heated to 80° C., and then allowed to react for 3 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 157 mL of ethanol was slowly added to a slurry solution including the crystallized product to further crystallize the product. The crystallized product was separated and then washed with 52 mL of ethanol, and dried at 50° C. to obtain L-homoserine crystals.

A recovery rate of L-homoserine was 45.9%, and purity thereof was 98.0%.

Comparative Example 2: Hydrochloric acid catalyst of 3.06 equivalents

Cells were removed from a fermentation broth, of which culture had been completed, through a membrane filter, and an aqueous solution including O-acetyl-L-homoserine was obtained.

300 mL of the aqueous solution including O-acetyl-L-homoserine (O-acetyl-L-homoserine concentration: 186 g/L, 346.2 mmol) was supplied to a reactor, and then 187.3 mL (1,059.5 mmol, 3.06 eq) of 6 N HCl was slowly added to the reactor to prepare a reaction solution at pH of 0.1 to 1.0. The prepared reaction solution was heated to 80° C., and then allowed to react for 3 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 1460 mL of ethanol was slowly added to a slurry solution including the crystallized product to further crystallize the product. The crystallized product was separated and then washed with 490 mL of ethanol, and dried at 50° C. to obtain L-homoserine crystals.

A recovery rate of L-homoserine was 52.7%, and purity thereof was 98.1%.

Comparative Example 3: Sulfuric acid catalyst of 1.07 equivalents

Cells were removed from a fermentation broth, of which culture had been completed, through a membrane filter, and an aqueous solution including O-acetyl-L-homoserine was obtained.

40 mL of the aqueous solution including O-acetyl-L-homoserine (O-acetyl-L-homoserine concentration: 300 g/L, 74.5 mmol) was supplied to a reactor, and then 4.3 mL (79.3 mmol, 1.07 eq) of 98% $H_2SO_4$ was slowly added to the reactor to prepare a reaction solution at pH of 0.1 to 1.0. The prepared reaction solution was heated to 80° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 132 mL of ethanol was slowly added to a slurry solution including the crystallized product to further crystallize the product. The crystallized product was separated and then washed with 44 mL of ethanol, and dried at 50° C. to obtain L-homoserine crystals.

A recovery rate of L-homoserine was 44.7%, and purity thereof was 98.0%.

Comparative Example 4: Sulfuric acid catalyst of 3.06 equivalents

Cells were removed from a fermentation broth, of which culture had been completed, through a membrane filter, and an aqueous solution including O-acetyl-L-homoserine was obtained.

330 mL of the aqueous solution including O-acetyl-L-homoserine (O-acetyl-L-homoserine concentration: 300 g/L, 620.5 mmol) was supplied to a reactor, and then 103.8 mL (1,898.7 mmol, 3.06 eq) of 98% $H_2SO_4$ was slowly added to the reactor to prepare a reaction solution at pH of 0.1 to 1.0. The prepared reaction solution was heated to 80° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 1300 mL of ethanol was slowly added to a slurry solution including the crystallized product to further crystallize the product. The crystallized product was separated and then washed with 430 mL of ethanol, and dried at 50° C. to obtain L-homoserine crystals.

A recovery rate of L-homoserine was 55.9%, and purity thereof was 98.1%.

Comparative Example 5: Acetic acid catalyst of 1.03 equivalents

Cells were removed from a fermentation broth, of which culture had been completed, through a membrane filter, and an aqueous solution including O-acetyl-L-homoserine was obtained.

40 mL of the aqueous solution including O-acetyl-L-homoserine (O-acetyl-L-homoserine concentration: 300 g/L, 74.5 mmol) was supplied to a reactor, and then 4.4 mL (76.7 mmol, 1.03 eq) of 99% acetic acid was slowly added to the reactor to prepare a reaction solution at pH of 1.0 to 2.0. The prepared reaction solution was heated to 80° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 132 mL of ethanol was slowly added to a slurry solution including the crystallized product to further crystallize the product. The crystallized product was separated and then washed with 44 mL of ethanol, and dried at 50° C. to obtain L-homoserine crystals.

A recovery rate of L-homoserine was 6.2%, and purity thereof was 98.0%.

Comparative Example 6: Acetic acid catalyst of 3.06 equivalents

Cells were removed from a fermentation broth, of which culture had been completed, through a membrane filter, and an aqueous solution including O-acetyl-L-homoserine was obtained.

1030 mL of the aqueous solution including O-acetyl-L-homoserine (O-acetyl-L-homoserine concentration: 320 g/L, 620.5 mmol) was supplied to a reactor, and then 108.5 ml (1898.7 mmol, 3.06 eq) of 99% acetic acid was slowly added to the reactor to prepare a reaction solution at pH of 1.0 to 2.0. The prepared reaction solution was heated to 80° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 1300 mL of ethanol was slowly added to a slurry solution including the crystallized product to further crystallize the product. The crystallized product was separated and then washed with 430 mL of ethanol, and dried at 50° C. to obtain L-homoserine crystals.

A recovery rate of L-homoserine was 5%, and purity thereof was 98.7%.

Example 1

Solid Resin Catalyst (Amberlyst-15 resin), Batch Type

Cells were removed from a fermentation broth, of which culture had been completed, through a membrane filter, and an aqueous solution including O-acetyl-L-homoserine was obtained.

40 mL of the aqueous solution including O-acetyl-L-homoserine (O-acetyl-L-homoserine concentration: 300 g/L, 74.5 mmol) was supplied to a reactor, and then 74.46 g (74.5 mmol, 1 eq) of a solid cation exchange resin (Amberlyst-15 resin) was added to the reactor to prepare a reaction solution at pH of 2.0 to 3.0. The prepared reaction solution was heated to 85° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 120 mL of ethanol was slowly added to a slurry solution including the crystallized product to further crystallize the product. The crystallized product was separated from the solid cation exchange resin and then washed with 400 mL of ethanol, and dried at 50° C. to obtain L-homoserine crystals.

A recovery rate of L-homoserine was 72%, and purity thereof was 99.3%.

Properties of Amberlyst-15 resin used as the solid cation exchange resin are as follows:
a) Physical properties
Copolymer: styrene-divinylbenzene
Matrix: macroporous
Type: strong acid cation
Functional group: sulfonic acid
Physical morphology: gray, opaque, spherical bead
b) Nitrogen BET
Surface area: 53 m$^2$/g
Total pore volume: 0.40 cc/g
Average pore diameter: 300 Å
c) Chemical properties
Ionic form as shipped: H$^+$
Concentration of acid site: 4.70 eq/kg (dry weight capacity 4.70 eq/kg)
Catalyst volatilities: 1.6%
d) Particle size
<300 um: ≤0.5%
<425 um: ≤2.0%
e) Swelling (in solvent)
Phenol: 38%
f) Density
Shipping weight: 610 g/L Example 2

Solid Resin Catalyst (Amberlyst-15 Resin), Batch Type

Cells were removed from a fermentation broth, of which culture had been completed, through a membrane filter, and an aqueous solution including O-acetyl-L-homoserine was obtained.

3,000 mL of the aqueous solution including O-acetyl-L-homoserine (O-acetyl-L-homoserine concentration: 100 g/L, 1,861.5 mmol) was supplied to a reactor, and then 1,861.5 g (1,861.5 mmol, 1 eq) of a solid cation exchange resin (Amberlyst-15 resin) was added to the reactor to prepare a reaction solution at pH of 4.5. The prepared reaction solution was heated to 85° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 9000 mL of ethanol was slowly added to a slurry solution including the crystallized product to further crystallize the product. The crystallized product was separated from the solid cation exchange resin and then washed with 3,000 mL of ethanol, and dried at 50° C. to obtain L-homoserine crystals.

A recovery rate of L-homoserine was 73.2%, and purity thereof was 99.1%.

Example 3

Solid Resin Catalyst (Amberlyst-15 Resin), Batch Type

Cells were removed from a fermentation broth, of which culture had been completed, through a membrane filter, and an aqueous solution including O-acetyl-L-homoserine was obtained.

1280 mL of the aqueous solution including O-acetyl-L-homoserine (O-acetyl-L-homoserine concentration: 185 g/L, 1,471.6 mmol) was supplied to a reactor, and then 1471.6 g (1,471.6 mmol, 1 eq) of a solid cation exchange resin (Amberlyst-15 resin) was added to the reactor to prepare a reaction solution at pH of 4.5. The prepared reaction solution was heated to 85° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 3,840 mL of ethanol was slowly added to a slurry solution including the crystallized product to further crystallize the product. The crystallized product was separated from the solid cation exchange resin and then washed with 1,470 mL of ethanol, and dried at 50° C. to obtain L-homoserine crystals.

A recovery rate of L-homoserine was 71.5%, and purity thereof was 99.0%.

Example 4

Solid Resin Catalyst (Purolite CT275 Resin), Batch Type

Cells were removed from a fermentation broth, of which culture had been completed, through a membrane filter, and an aqueous solution including O-acetyl-L-homoserine was obtained.

300 mL of the aqueous solution including O-acetyl-L-homoserine (O-acetyl-L-homoserine concentration: 100 g/L, 186.2 mmol) was supplied to a reactor, and then 186.2 g (186.2 mmol, 1 eq) of a solid cation exchange resin (Purolite CT275 resin) was added to the reactor to prepare a reaction solution at pH of 4.5. The prepared reaction solution was heated to 85° C., and then allowed to react for 5 hr. Completion of the reaction was confirmed by HPLC.

After the reaction was completed, a solution including a product was transferred to an enrichment tube, and then concentrated at a concentration of 480 g/L to prepare a concentrate. The concentrate was transferred to an ageing tank, and then cooled to 25° C. to crystallize the product. 900 mL of ethanol was slowly added to a slurry solution including the crystallized product to further crystallize the product. The crystallized product was separated from the solid cation exchange resin and then washed with 300 mL of ethanol, and dried at 50° C. to obtain L-homoserine crystals.

A recovery rate of L-homoserine was 81.6%, and purity thereof was 99.4%.

Properties of Purolite CT275 resin used as the solid cation exchange resin are as follows:

Polymer structure: macroporous polystyrene crosslinked with divinylbenzene

Appearance: spherical beads

Functional group: sulfonic acid

Ionic form: $H^+$ form

Dry weight capacity (min.) 5.2 eq/kg ($H^+$ form)

Moisture retention: 51-59% ($H^+$ form)

Partice size range: 425-1200 um

<425 um (max.): 1%

Uniformity coefficient (max.): 1.7

Surface area: 20-40 $m^2$/g

Pore volume: 0.4~0.6 mL/g

Median pore diameter: 400~700 Å

Surface acidity acid strength: 60 kJ/mol

Specific gravity: 1.2

Shipping weight (approx.): 755~790 g/L (47.2~49.4 $lb/ft^3$)

Temperature limit: 130° C. (266.0° F.)

Example 5

Solid Resin Catalyst (Purolite CT275 Resin), Continuous Type

Cells were removed from a fermentation broth, of which culture had been completed, through a membrane filter, and an aqueous solution including O-acetyl-L-homoserine was obtained.

300 mL of the aqueous solution including O-acetyl-L-homoserine (O-acetyl-L-homoserine concentration: 100 g/L, 186.2 mmol) was continuously supplied to a lower portion of a resin tower at a constant rate, and then the solution including the reaction product was discharged from an upper portion of the resin tower at the same rate.

The interior of the resin tower was filled with 186.2 g (186.2 mmol, 1 eq) of Purolite CT275 resin, and pH and temperature of the interior of the resin tower were 3.2 and 85° C., respectively. The time for the aqueous solution to pass through the resin tower was 5 hr. Completion of the reaction in the solution including the reaction product was confirmed by HPLC.

The solution including the product discharged from the resin tower was transferred to an enrichment tube, and then concentrated at a concentration of 480 g/L to prepare a concentrate. The prepared concentrate was transferred to an ageing tank, and then cooled to 25° C. to crystallize the product.

900 mL of ethanol was slowly added to a slurry solution including the crystallized product to further crystallize the product.

The crystallized product was separated using a separator. The separated product was washed with 300 mL of ethanol, and dried in a dryer at 50° C. to obtain L-homoserine crystals.

A recovery rate of L-homoserine was 81.6%, and purity thereof was 99.4%.

The reaction conditions, the kinds of the catalysts, the recovery rates, etc. in Comparative Examples 1 to 6 and Examples 1 to 5 are shown in Table 1 below.

Purity is the content of the product from which solid impurities other than homoserine are excluded.

Recovery rate is a ratio of actually produced L-homoserine to a theoretical value of L-homoserine obtained from introduced L-homoserine derivative.

TABLE 1

| | Acid catalyst | Reaction type | Content of acid catalyst [eq.] | Concentration of aqueous solution including L-homoserine derivative to be supplied [g/L] | Recovery rate [%] | Purity [%] |
|---|---|---|---|---|---|---|
| Comparative Example 1 | HCl | Batch type | 1.02 | 300 | 45.9 | 98.0 |
| Comparative Example 2 | HCl | Batch type | 3.06 | 186 | 52.7 | 98.1 |
| Comparative Example 3 | $H_2SO_4$ | Batch type | 1.07 | 300 | 44.7 | 98.0 |
| Comparative Example 4 | $H_2SO_4$ | Batch type | 3.06 | 300 | 45.9 | 98.1 |
| Comparative Example 5 | $CH_3COOH$ | Batch type | 1.03 | 300 | 6.2 | 98.0 |
| Comparative Example 6 | $CH_3COOH$ | Batch type | 3.06 | 320 | 5.0 | 98.7 |
| Example 1 | Amberlyst-15 resin | Batch type | 1.00 | 300 | 72.0 | 99.3 |
| Example 2 | Amberlyst-15 resin | Batch type | 1.00 | 100 | 73.2 | 99.1 |
| Example 3 | Amberlyst-15 resin | Batch type | 1.00 | 185 | 71.5 | 99.0 |
| Example 4 | Purolite CT275resin | Batch type | 1.00 | 100 | 81.6 | 99.4 |
| Example 5 | Purolite CT275resin | Continuous type | 1.00 | 100 | 81.6 | 99.4 |

As shown in Table 1, according to the methods of using the solid acid catalysts of Examples 1 to 5, the recovery rate and purity of L-homoserine were improved, as compared with the methods of using the liquid acid catalysts of Comparative Examples 1 to 6. Further, as compared with Examples 1 to 4, the continuous type preparation method of Example 5 enables continuous production of L-homoserine, and thus production efficiency was further improved, and recycling of the resin catalyst was possible only by changing the composition of the supply solution without separation and purification of the resin catalyst, and as a result, there is an additional effect of reducing the maintenance costs.

INDUSTRIAL AVAILABILITY

According to a method of preparing L-homoserine, it is possible to simply prepare L-homoserine with high purity at a high recovery rate by using a solid acid catalyst.

Further, according to the method of preparing L-homoserine, production efficiency is remarkably improved, recycling of the catalyst is easy, and maintenance costs are reduced, thereby securing economic efficiency.

The invention claimed is:

1. A method of preparing L-homoserine, the method comprising:
   contacting an L-homoserine derivative represented by the following Formula 1 with a solid acid catalyst:

<Formula 1>

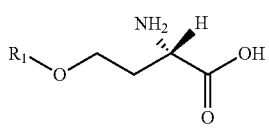

in Formula 1,
$R_1$ is $R_a$—(C=O)—, $R_a$ is a substituted or unsubstituted alkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted cycloalkyl group having 3 to 10 carbon atoms, a substituted or unsubstituted aryl group having 6 to 20 carbon atoms, or a substituted or unsubstituted heteroaryl group having 2 to 10 carbon atoms, and substituents of the alkyl group, the alkenyl group, the alkynyl group, the cycloalkyl group, the aryl group, and the heteroaryl group are each independently halogen, —COOH, —COCH_3, —NH_2, —NO_2, a —CN, an alkyl group having 1 to 6 carbon atoms, an aryl group having 6 to 10 carbon atoms, or a cycloalkyl group having 3 to 10 carbon atoms.

2. The method of claim 1, wherein $R_1$ is acetyl or succinyl.

3. The method of claim 1, wherein the contacting is contacting the L-homoserine derivative represented by Formula 1 with an aqueous solution comprising water and the solid acid catalyst.

4. The method of claim 1, wherein the solid acid catalyst comprises a resin catalyst.

5. The method of claim 4, wherein the solid acid catalyst comprises a cation exchange resin catalyst.

6. The method of claim 5, wherein the cation exchange resin catalyst comprises one or more acidic functional groups selected from —SO_3H and —COOH.

7. The method of claim 5, wherein the cation exchange resin catalyst comprises a structure in which one or more acidic functional groups selected from —SO_3H and —COOH are linked to a polystyrene-divinylbenzene copolymer.

8. The method of claim 4, wherein the contacting is carried out in a resin tower comprising the solid acid catalyst.

9. The method of claim 1, wherein a content of the solid acid catalyst is 0.1 equivalent to 10 equivalents with respect to 1 equivalent of the L-homoserine derivative represented by Formula 1.

10. The method of claim 3, wherein the aqueous solution comprising water and the solid acid catalyst is at pH of 1 to 5.

11. The method of claim 1, wherein the contacting is carried out at a temperature of 20° C. to 150° C.

12. The method of claim 1, wherein the contacting is carried out for 0.1 hr to 20 hr.

13. The method of claim 1, wherein the contacting comprises:
   supplying the L-homoserine derivative represented by Formula 1;
   producing L-homoserine by contacting the L-homoserine derivative represented by Formula 1 with the solid acid catalyst; and
   discharging the L-homoserine.

14. The method of claim 13, wherein the supplying the L-homoserine derivative represented by Formula 1 and the discharging L-homoserine are continuously carried out.

15. The method of claim 1, the method further comprising:
   collecting the L-homoserine.

\* \* \* \* \*